United States Patent [19]

Sakamoto

[11] Patent Number: 4,473,298
[45] Date of Patent: Sep. 25, 1984

[54] METHOD FOR MEASURING A HALFTONE DOT AREA RATE OR A HALFTONE PICTURE DENSITY

[75] Inventor: Takashi Sakamoto, Kyoto, Japan

[73] Assignee: Dainippon Screen Seizo Kabushiki Kaisha, Kyoto, Japan

[21] Appl. No.: 258,899

[22] Filed: Apr. 30, 1981

[30] Foreign Application Priority Data

May 1, 1980 [JP] Japan ................................ 55-57083

[51] Int. Cl.³ ............................................ G01N 21/01
[52] U.S. Cl. ..................................... 356/432; 356/445
[58] Field of Search ....................... 356/430, 432–434, 356/443–445

[56] References Cited

U.S. PATENT DOCUMENTS 3,053,181  9/1962  Jorgensen ............................ 356/445
3,375,751  4/1968  Engborg et al. ..................... 356/443
3,393,602  7/1968  Stouffer ................................ 356/445
4,264,210  4/1981  Mitsuhashi ......................... 356/432
4,371,265  2/1983  Mitsuhashi ......................... 356/432

Primary Examiner—Bruce Y. Arnold
Attorney, Agent, or Firm—Michael A. Painter

[57] ABSTRACT

A method for measuring a halftone dot area rate, i.e. a halftone picture density, in a densitometer or halftone dot area rate measuring means. A light beam is emitted by a light source and impinges upon an object to be measured. The light beam passes through or is reflected from the object to be measured and is received by a photoelectric element. An aperture diameter is selected such that, when the halftone dot area rate in a reference surface which has a screen pitch equal to that of the measured surface is approximately 50%, the ratio of the area of the dark portions to the area of the light portions of the halftone dots included within the aperture diameter, i.e. the measured surface, is substantially 1:1.

3 Claims, 5 Drawing Figures

METHOD FOR MEASURING A HALFTONE DOT AREA RATE OR A HALFTONE PICTURE DENSITY

BACKGROUND OF THE INVENTION

The present invention relates to a method and device for measuring a halftone dot area rate or halftone picture density in a densitometer or halftone dot area rate measuring apparatus.

In a conventional halftone dot area rate measuring means, since the graduation of a measured halftone picture image varies the aperture diameter which will determine the measured area is preferably small. However, if it is too small, when the halftone picture image is measured, the value which is measured will vary depending on the relative position of the aperture and the halftone dot.

Large variances do not arise when the number of scanning lines per distance increment is large. Large variances often occur when the number of scanning lines is small, e.g., a gauge having about ten lines per centimeter for printed matter. Such a gauge is printed in a relatively small area such as 5 mm×6 mm, and hence this problem can be resolved only by expanding the diameter of the aperture or the measuring area.

SUMMARY OF THE INVENTION

It is an object of the present invention to provide a method for measuring a halftone dot area rate or halftone picture density in a densitometer or halftone dot area rate measuring means free from the aforementioned inconveniences, which is accurate, stable and reliable, and which is capable of measuring an area which is small when compared with the screen pitch.

It is another object of the present invention to provide a device for measuring a halftone dot area rate or halftone picture density in a densitometer or halftone dot area rate measuring means free from the aforementioned inconveniences, which is accurate, stable and reliable, and which is capable of measuring an area which is small when compared with the screen pitch.

According to the present invention there is provided a method for measuring a halftone dot area rate or halftone picture density in a densitometer or halftone dot area rate measuring means. Pursuant to the present invention, a light beam generated by a light source is incident to an object to be measured. The light beam is passed through or is reflected from the object and is received by a photoelectric element. When the object being measured has a halftone dot area rate of approximately 50%, the measured area of the object is determined so that the ratio between the dark and the light portions of the halftone dots included in the measured area of the object is substantially the same as the halftone dot area rate.

The present invention constitutes a device for measuring a halftone dot area rate or halftone picture density in a densitometer or halftone dot area rate measuring means. A light beam generated by a light source is incident to an object to be measured, and the light beam passed through or reflected by the object is received by a photoelectric element. The present invention determines the measuring area of the object with respect to a proper value for the screen pitch of the object.

BRIEF DESCRIPTION OF THE DRAWINGS

Other objects and features of the present invention will be clear from the following description of the preferred embodiment of the present invention with reference to the accompanying drawings, in which:

FIG. 4a—the center of the aperture is coincident with the center of a dark part of the halftone dots, and FIG. 4b—the center of the aperture is coincident with the center of a light part of the halftone dots.

DESCRIPTION OF THE PRESENTLY PREFERRED EMBODIMENTS

Figure 1:
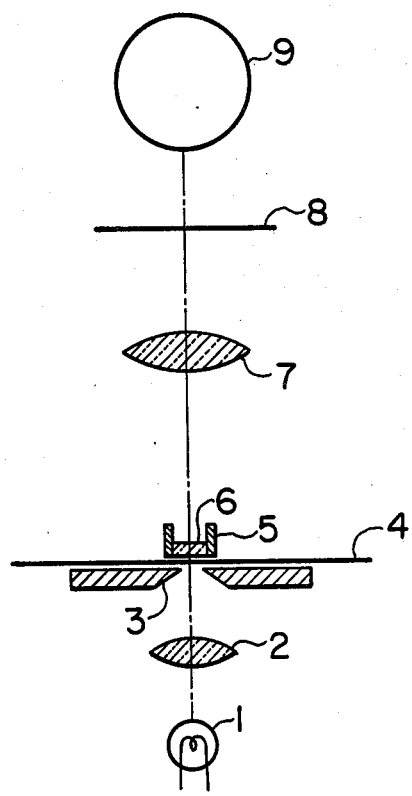
FIG. 1 is a schematic view of an optical system for a transmission densitometer or halftone dot area rate measuring means to be used according to the present invention.

FIG. 1 illustrates the optical system of a transmission densitometer or halftone dot area rate measuring means according to the present invention. The apparatus shown in FIG. 1 comprises: a light source 1 such as an incandescent lamp, a first condenser lens 2, an aperture plate 3 made of a light shielding material having an aperture therethrough, a diffusion plate 6 surrounded by a guide 5 which prevents the ambient light from coming in, a second condenser lens 7, a filter 8 for correcting spectral characteristics, and a photoelectric element 9 such as a photomultiplier. All are aligned along the light axis. The object 4 to be measured is disposed between guide 5 and aperture plate 3. The aperture edge of the aperture plate 3 is tapered away from the light source 1 and it is adapted to be formed so that a luminous energy distribution over a measured surface may be uniform regardless of the thickness of aperture plate 3.

In this embodiment, the light beam generated by the light source 1 is converged by the first condenser lens 2 and then passes through the aperture of the aperture plate 3. The measuring area is determined by the aperture. The light beam emitted through the aperture then passes through the object 4. The luminous energy of the light beam is decreased depending on the transmittance of the object 4 when it passes through the object. After passing through object 4, the attenuated light beam is directed to the receiving section. In the light receiving section, the ambient light is prevented from coming therein by the guide 5 and thus only the light beam through the aperture is incident. The light beam is diffused in the diffusion plate 6 and a space of light shield tube (not shown). Then, the diffused light beam is converged by the second condenser lens 7 and its spectral characteristics are corrected by the filter 8. Finally, the corrected light beam is incident to the photoelectric element 9.

The photoelectric current which is proportional to the transmittance of the object 4, is obtained in the photoelectric element 9. When the photoelectric current is fixed, the photoelectric voltage obtained in the photoelectric element 9 is proportional to the transmission of the object 4. Thus the photoelectric current or voltage which is obtained is then converted into a halftone dot area rate, i.e. a halftone picture density.

Figure 2:
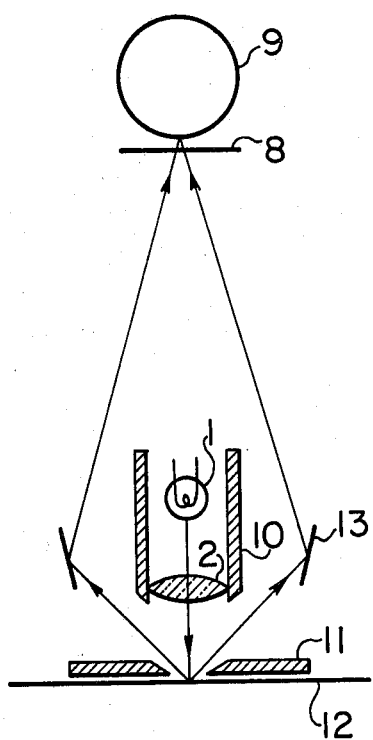
FIG. 2 is a schematic view of an optical system for a reflection densitometer or halftone dot area rate measuring means to be used according to the present invention.

An optical system employing a reflection densitometer or halftone dot area rate measuring means is shown in FIG. 2. The object 12 to be measured is aligned with: an aperture plate 11 having an aperture therethrough, the aperture plate 11 having the same shape and functions as that shown in FIG. 1; the condenser lens 2 and the light source 1; a light shield tube 10 for shielding the light generated by the light source 1; the correction filter 8; and the photoelectric element 9. All are aligned along the light axis so that the frustum tubular mirror 13 may reflect to the photoelectric element 9 via the filter 8 the light beam which is incident from the light source 1 to the object 12, and is then reflected by the object 12 in a manner similar to that described above.

In this embodiment, when the light beam is reflected by the object 12, the luminous energy of the light beam decreases depending on the reflectance of the object.

As described above, the photoelectric current is obtained in the photoelectric element 9 proportional to the reflectance of the object 17. When the photoelectric current is fixed, the photoelectric voltage obtained in the photoelectric element 9 is proportional to the reflection of the object 17. Thus the obtained photoelectric current or voltage is then converted into the halftone dot area rate or the halftone picture density, in the same manner as described above.

Figure 4:
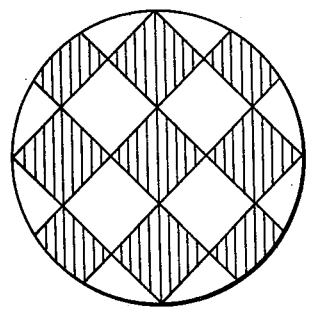
FIGS. 4 and 5 show the positional relationship between the aperture and the halftone dots.
Figure 5:
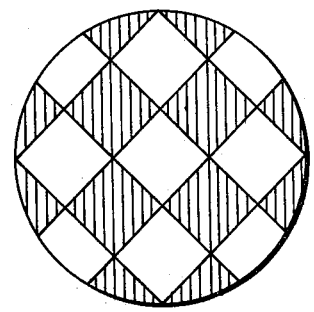
Figure 3:
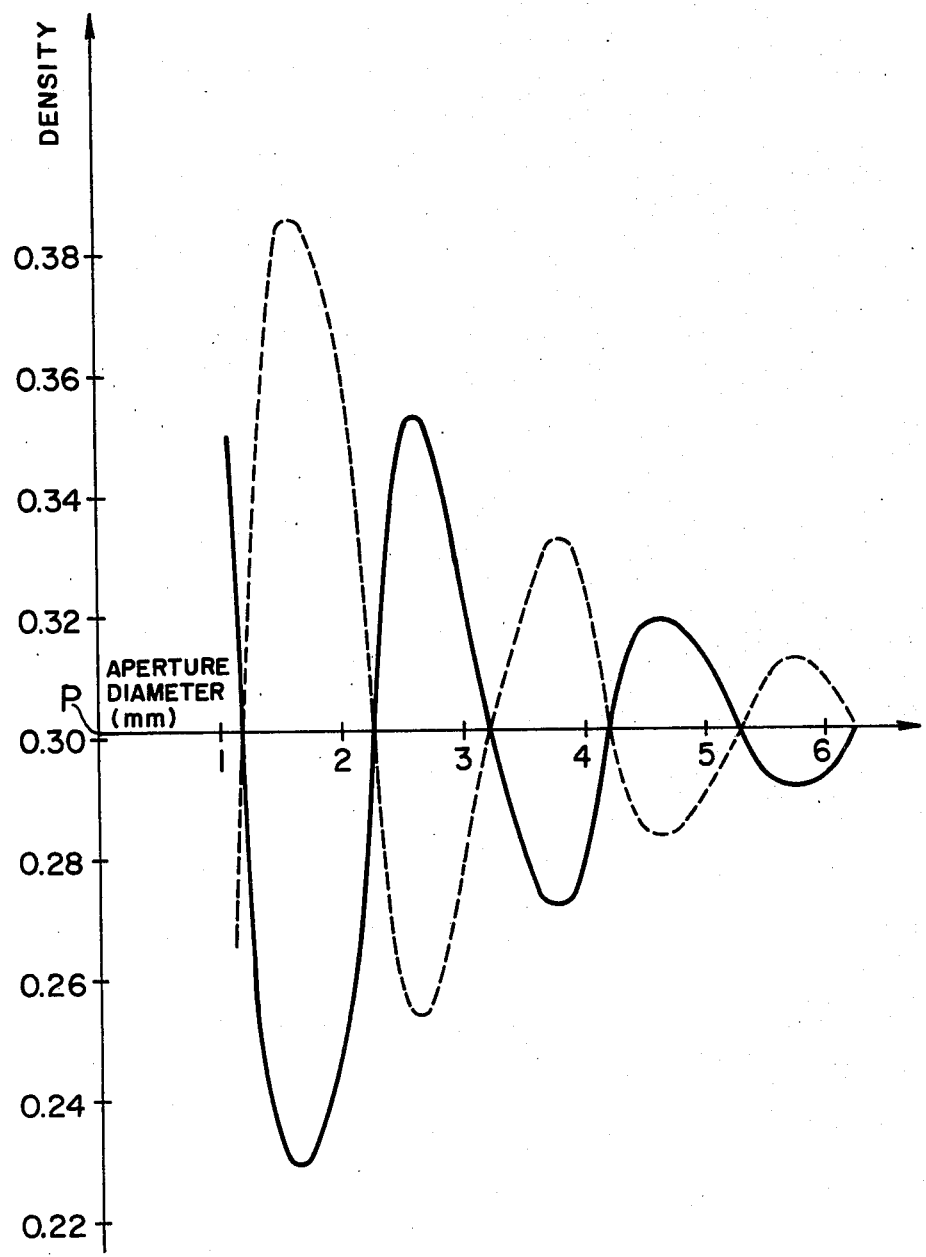
FIG. 3 shows density value curves of a halftone dot having a screen pitch of one millimeter and a halftone dot area rate of 50%, plotted with respect to an aperture diameter, solid and broken lines indicated the positional relationship between the aperture and the halftone dots, as shown in FIGS. 4 and 5, respectively.

FIG. 3 illustrates the density value curves of halftone dots having a screen pitch of one millimeter and a halftone dot area rate of 50%. The curves are obtained by varying the diameter of the aperture 3 or 11. The curve represented by a solid line is obtained when the center of the aperture is coincident with the center of a dark portion of the halftone dot, and the curve represented by a broken line is obtained when the center of the aperture is coinicident with the center of a light portion of the halftone dot, as shown in FIGS. 4a and 4b, respectively. When the center of the aperture 3 or 11 is not coincident with the center of a dark or a light portion of the halftone dot, the density value of the halftone dot is a value intermediate between the two values shown in FIG. 3.

From FIG. 3, it is readily understood that the measured error of the halftone dot density becomes zero periodically. When the halftone dot possesses a square shape, an aperture diameter, A, at which the measured error is zero, can be expressed as a function of the screen pitch P by the following formula (1) wherein n means a positive integral number.

$$A = P \times (n + 0.25) \quad (1)$$

The values of A and P are measured in millimeters. This means that when halftone dots having a halftone dot area rate of 50% are reproduced, a group of aperture diameter values exist of which the ratio of the dark to the light portions of the halftone dot pattern is unity.

Further, when the aperture 3 or 11 employs one of such diameter values, it has been ascertained that, even when the center of the aperture is not coincident with the dark or the light portion of the halftone dot, the dispersion of the measured values is very small.

In a densitometer or halftone dot area rate measuring device having an optical system of the scanning type for a TV camera, or the like, means for improving or eliminating measured errors may be applied to the optical system. Further, in a system wherein the photoelectric signals obtained in the above device are digitized and then the digital signals arithmetically processed by using a microcomputer, or the like, when the screen pitch is varied, the halftone picture data area corresponding to the measured area to be processed is set at an optimum value. The value depends on the screen pitch so as to reduce or improve the measured error when the desnity or the halftone dot area rate is measured. When a method is employed which uses a device of the scanning type, high costs may be incurred. According to the present invention, in principle, an optical system for a conventional densitometer or halftone dot area rate measuring means is used.

When measuring a gauge for printed matter having a screen pitch of one millimeter (ten lines per centimeter) the problem of the dispersion of the errors of the measured values is most serious. According to the present invention in order to eliminate or minimize the dispersion of the errors of the measured values, a proper aperture size or diameter of the aperture plate is determined.

When the screen pitch is one millimeter, a proper aperture diameter such as 1.25, 2.25, 3.25 or 4.25 mm is determined according to the equation (1) described above.

When the screen pitch is 0.391 millimeter (25.6 lines per centimeter), a proper aperture diameter such as 1.27, 1.66, 2.05, 2.44, 2.83, 3.23, 3.62, 4.01, 4.40 or 4.79 mm is determined in accordance with the equation (1) for positive integer values of in from 1 to 12, inclusive.

When the screen pitch is less than 0.245 millimeter (39.4 lines per centimeter), the aperture diameter may be determined to a proper value such as 3 or 5 millimeters. In this case, a relatively large number of halftone dots are included in the measured surface, and hence the dispersion of the measured values can be reduced to a substantially negligible amount.

Several examples of the aperture diameters with respect to the screen pitches are tabulated in the following.

TABLE

| Screen Pitch: mm (lines/cm) | 1 (10) | 0.391 (25.6) | 0.299 (33.5) | less than 0.254 (more than 39.4) |
|---|---|---|---|---|
| Aperture Diameter: mm Example A | 2.25 | 2.44 | 2.17 | 5 |
| Example B | 3.25 | 3.23 | 3.36 | 5 |
| Example C | 4.25 | 4.40 | 4.26 | 5 |

With respect to Example C, aperture plates with apertures having diameters of 4.25, 4.40, 4.26 and 5 mm and a screen pitch of 1, 0.391, 0.299 and less than 0.254 mm of the gauges, respectively are prepared in advance. The aperture plate 3 or 11 is exchanged depending on the screen pitch of the gauge to be measured. Then, the density or the halftone dot area rate of the gauge is measured.

An aperture having a diameter equal to the arithmetic mean value 4.33 mm of the two aperture diameters 4.25 and 4.40 mm for the respective screen pitches 1 and 0.39 mm, respectively can be used in common for these two. Another aperture having a diameter equal to the weighted average value 4.29 mm of these two diameters can also be used in common. Further, an aperture having a diameter equal to the weighted average value 4.31 mm of the three diameters 4.25, 4.40 and 4.26 for the respective screen pitches 1, 0.391 and 0.299 mm can be employed in common for these three. With emphasis on the larger screen pitch, the diameter for these three may be represented by 4.25 mm, viz., the aperture diameter 4.25 mm is used when the screen pitch is at least 0.254 mm, and the aperture diameter 5 mm is used when the screen pitch is less than 0.254 mm.

Furthermore, when the screen pitch is at most one millimeter, the aperture diameter may be always represented by 4.25 mm for the largest screen pitch of one millimeter. In this case, since the density value curves of FIG. 3 are damped oscillation curves, when the screen pitch is one millimeter and n is selected to four or so, for the other screen pitches n becomes at least ten. Consequently, when n equals at least ten for the other screen pitches, the dispersion of the measured values is largely reduced.

Thus, even when the aperture diameter deviates from the proper value, the dispersion of the measured values is decreased to a negligible amount.

Alternatively, a diaphragm can be applied to the aperture of the aperture plate 3 or 11 so that a proper aperture diameter may be selected depending on the screen pitch or a screen line number of an object to be measured. The screen pitch or the screen line numbers can be marked on the corresponding diameters of the diaphragm.

According to the present invention, objects having a large screen pitch such as one millimeter (10 lines/cm), and 2.54 millimeters (4 lines/cm) can sufficiently be measured.

The present invention has been described with reference to preferred embodiments thereof; various changes and modifications can be made by a person skilled in the art without departing from the scope of the present invention.

What is claimed is:

1. A method for measuring a halftone dot area rate i.e. halftone picture density, by using a densitometer or halftone dot area rate measuring means comprising the steps of:
   (a) emitting a light beam generated by a light source to an object to be measured;
   (b) receiving the light beam passed through or reflected from the object by a photoelectrical element; and
   (c) selecting an aperture diameter through which said object is measured such that when the halftone dot area rate in a reference surface which has a screen pitch equal to that of the measured surface, is approximately 50%, the ratio of the area of the dark portions to the area of the light portions of the halftone dots included in the measured surface is substantially 1:1.

2. A method as defined in claim 1, wherein the measured area of the object is determined by using an aperture plate which has an aperture diameter proportional to the screen pitch of the object.

3. A method as defined in claim 2, wherein the aperture diameter is determined according to the equation expressed below, wherein A is the aperture diameter measured in millimeters, P is the screen pitch measured in millimeters, and n is a positive integer:

$$A = P \times (n + 0.25)$$

* * * * *